United States Patent [19]

Sugimoto et al.

[11] 4,276,282

[45] Jun. 30, 1981

[54] INTERFERON AND PREPARATIONS CONTAINING INTERFERON

[75] Inventors: Kaname Sugimoto; Shokichi Yuen, both of Okayama, Japan

[73] Assignees: Ken Hayashibara, Okayama; Shin Ashida, Hyogo, both of Japan

[21] Appl. No.: 5,585

[22] Filed: Jan. 22, 1979

[30] Foreign Application Priority Data

Jan. 22, 1978 [JP] Japan ................................. 53-5368
Oct. 31, 1978 [JP] Japan ............................... 53-134026

[51] Int. Cl.³ ...................... A61K 45/02; A61K 39/00
[52] U.S. Cl. ...................................... 424/85; 435/68; 435/811
[58] Field of Search ..................... 424/85; 435/68, 811

[56] References Cited

PUBLICATIONS

Chemical Abstracts, vol. 89, 105634a, 1978.
Chemical Abstracts, vol. 82, 14962v, 1975.
Chemical Abstracts, vol. 83, 25879v, 1975.
Miyoshi, I., et al., Cancer, vol. 40, pp. 2999–3003, 1977.
Miyoshi, I., et al., Nature, vol. 267, pp. 843–844, 1977.
Strander, H., et al., J. of Clin. Microbiol., vol. 1, pp. 116–117, 1975.
Finter, "Interferons," 1966, pp. 263–266, North Holland Pub. Co.
Miyoshi et al., Reprint from "Nature," vol. 267, No. 5614 (1977), pp. 843–844.
Science, vol. 204, pp. 1184–1185, Editorial, 1979.
Proteins, Nucleic Acid and Enzyme, vol. 21, No. 4, pp. 616–643, "The Current Situation of the Maintenance and Preservation of Tissue Culture Cell Lines in Japan".

*Primary Examiner*—Delbert R. Philips
*Assistant Examiner*—Blondel Hazel
*Attorney, Agent, or Firm*—Browdy and Neimark

[57] ABSTRACT

The present invention relates to processes for an easily applicable industrial production of interferon and the possibilities of the products for preventing and treating interferonsensitive diseases.

The process easily produces a large amount of interferon and transplanting established human cells to other warm-blooded animals or inoculating the cells in a diffusion chamber and multiplying the cells therein while allowing the animals to supply the cells with their nutrient body fluids, then exposing in vivo or in vitro the resultant cells to the action of interferon inducer. The present invention is also based on the discovery that the interferon obtained by the present method is an effective and superior preparation for preventing and treating interferon-sensitive diseases.

8 Claims, No Drawings

INTERFERON AND PREPARATIONS CONTAINING INTERFERON

FIELD OF THE INVENTION

The present invention relates to interferon and preparations containing interferon for preventing and treating interferon-sensitive diseases.

BACKGROUND OF THE INVENTION

As described by Shigeyasu Kobayashi, ["Interferon" (1975), published by Kodansha, Ltd., Tokyo], by D. A. J. Tyrrell, ["Interferon and Its Clinical Potential" (1976), published by William Heinemann Medical Books, Ltd., London] and in "Protein, Nucleic Acid and Enzyme", vol. 21, no. 4 (1976), published by Kyoritsu Shuppan Co., Ltd., Tokyo, interferon is a term to define a substance which is a proteinaceous substance induced intracellularly or extracellularly by living cells on exposing the cells to interferon inducers such as virus, bacterium, protozoa, rickettsia, nucleic acid, endotoxin and polysaccharide, and which has an activity to inhibit nonspecifically the multiplication of various viruses in the cells.

Based on this activity, interferon has been regarded as a promising preventive and therapeutic agent for viral diseases since it was discovered.

In recent years, the realization of interferon as a medicinal was in great expectation because it has been recognized as having antitumor activities on nonviral or viral tumor.

Since interferon is species specific, only interferon derived from living human cells is effective in the prevention and therapy of human diseases.

Conventionally, leucocytes were used as living human cells to prepare interferon. Leucocytes are obtained by separation from fresh blood, but their preservation and supply, in a large quantity and at a low cost, are extremely difficult.

Utilization of living cells obtained by inoculating established human cells to nutrient media and cultivating them in vitro was also attempted for the production of interferon. The in vitro methods, however, are impracticable on a large scale and at a low cost, having the disadvantages of requiring a large amount of human serum, and giving unstable multiplication, low multiplication rate and low cell concentration.

Due to the above situation, industrial production of interferon feasible for prevention and/or therapy of human diseases has not so far been realized.

SUMMARY OF THE INVENTION

With painstaking efforts, the present inventors have studied processes for an easily applicable industrial production of interferon and the possibilities of the products for preventing and treating interferon-sensitive diseases.

The efforts resulted in the discovery that instead of inoculating and culturing established human cells in culture medium in vitro, established human cells may be transplanted to other warm-blooded animals or the cells may be inoculated in a diffusion chamber and the cells multiplied therein, while allowing the animals to supply the cells with their nutrient body fluids, the resultant cells then being exposed in vivo or in vitro to the action of interferon inducer to easily produce a large amount of interferon. The present invention is also based on the discovery that the interferon obtained by the method disclosed herein is an effective and superior preparation for preventing and treating interferon-sensitive diseases.

In comparison with the conventional processes which are used for multiplying cells in vitro, the processes of the present invention have the advantages that they require no or much less nutrient medium supplemented with expensive human serum, that the multiplication of established cells can be maintained more easily, and that a higher interferon activity can be attained. More particularly, established human cells can be easily multiplied in other warm-blooded animal bodies by either transplanting the cells thereinto or inoculating a diffusion chamber containing the cells into an animal, fed in the usual way, while allowing the animal to supply the cells with its nutrient body fluid. Furthermore, in comparison with the conventional in vitro methods, the invention has the additional features that established human cells multiply more stably and rapidly and that a larger production of cells and a higher interferon yield per cell are attainable.

DETAILED DESCRIPTION OF PREFERRED EMBODIMENTS

Any established human cells are employable, so far as they can multiply easily when transplanted to other warm-blooded animal bodies. For example, established normal human cells such as OUMS-20 cell, OUMS-25 cell, HEF cell, HUF-2 cell and WI-38 cell, reported in "Protein, Nucleic Acid and Enzyme", vol. 20, no. 6, pp. 616–643 (1975), published by Kyoritsu Shuppan Co., Ltd., Tokyo, and established cells derived from human tumor cells such as Namalva cell, reported in "Journal of Clinical Microbiology", vol. 1, pp. 116–117 (1975), BALL-1 cell, TALL-1 cell, NALL-1 cell, reported by Isao Miyoshi, ["Nature" vol. 267, pp. 843–844 (1977)] and JBL-cell, reported by Isao Miyoshi, ["Cancer" vol. 40, no. 6, in press (1977)] are employable in the invention.

In the present invention, any warm-blooded animal can be used if established human cells can multiply easily therein; for example, fowls such as chick and pigeon, and mammals such as dog, cat, monkey, goat, pig, bovine, horse, rabbit, guinea pig, rat, hamster, normal mouse and nude mouse.

Since the animals are liable to effect undesirable immunoreactions when the established human cells are transplanted therein, it is preferable to use animals in the most possible immature forms, namely, egg, embryo, fetus, newborn and young animal, to exploit immunoparalysis.

Prior to transplantation of the cells, the animal may be pretreated either by irradiation with X-ray or γ-ray at 200–600 rem, or with antiserum or immunosuppressive agent to depress the immunoreactions.

Nude mouse is desirable as a warm-blooded animal because it effects no or low immunoreactions and established human cells can be transplanted and multiplied rapidly therein without pretreatments.

Multiplication of established human cells can be stabilized further by first transplanting the cells in hamster and then transplanting them in nude mice where interferon with increased activity is induced.

In this case, the multiplied cells are further transplantable from one warm-blooded animal body to another animal body of the same species, genus, class or division except human. Established human cells can be transplanted to any part of animal body as far as they multiply easily therein; for example, intravenously, intraperitoneally, subcutaneously and in allantoic cavity.

Instead of multiplying established human cells directly in animal bodies, established human cells can be inoculated and multiplied in a diffusion chamber which may be any of different shapes and sizes, fitted with a filter membrane with pores of about $10^{-7}$ to $10^{-5}$ in diameter, for example, membrane filter, ultrafilter or hollow fiber, and placing the chamber to animal bodies, for example, intraperitoneally, while allowing the animals to supply the cells with their nutrient body fluids.

If necessary, established human cells can be multiplied in the diffusion chamber while allowing the nutrient body fluid of the warm-blooded animal to circulate into and out of the nutrient medium in the chamber to supply the cells with the nutrient fluid. In this case, if the chamber is placed on the animal body, the multiplication state of the cells can be observed through the wall of the chamber, and the number of cells per animal can be increased further, without sacrificing unnecessarily the animal by successively removing the chamber, inoculating the cells in another chamber containing fresh nutrient medium therein and placing the latter chamber on the same animals.

The diffusion chamber method has the additional features that any warm-blooded animal except human is usable for multiplication of established human cells, that pretreatment for depression of immunoreactions is not required, and that established human cells multiplied in the chamber can be harvested easily without contamination by animal cells because the human cells do not contact directly with animal cells and there is no fear of the undesirable reactions.

After the transplantation of the human cells, the animal is fed in the usual manner without special treatment.

The multiplication period of established human cells is usually 1 to 20 weeks. If the established cells transplanted are those derived from human normal or tumoral leucocytes, the rate of cell multiplication is so high that the multiplication can be achieved usually in the period of 1 to 5 weeks.

The number of the multiplied human cells was counted and found as about $10^7$ to $10^{12}$ or more per animal.

In other words, the processes of the invention are extremely advantageous for producing interferon because the number of the cells transplanted or inoculated to the animal increases about $10^2$ to $10^7$-fold or more by the processes; about $10^1$ to $10^6$-fold or more than those attained by inoculating and multiplying the same cells in nutrient medium in vitro.

The multiplied living human cells may be induced by any method to produce interferon. The part of the animal body itself where the cells have been multiplied may be exposed to an interferon inducer. For example, interferon may be obtained by exposing directly the suspended-human cells that multiplied intraperitoneally or human tumor cells formed subcutaneously to interferon inducer to induce interferon, and collecting and purifying the induced interferon from the exposed human cells.

Interferon can also be induced by recovering the multiplied human cells from the animal bodies and exposing the cells to interferon inducer in vitro. For example, human cells obtained by collecting suspended-human cells that multiplied intraperitoneally or those obtained by dissociating isolated human massive tumor that formed subcutaneously in animal bodies, are suspended in a nutrient medium kept at about 20° to 40° C. to give a concentration of about $10^5$–$10^8$ cells per ml. Then, the cells are exposed to interferon inducer to induce interferon and the formed interferon is collected and purified.

When human cells are multiplied in diffusion chambers, the cells may be exposed to interferon inducers in the chambers or after recovering the cells from the chambers.

In the induction of interferon, the production of interferon can be increased further by known methods such as the priming method using interferon and the superinduction method using a metabolic inhibitor.

The interferon production per animal can be increased further by the following methods: (a) a method wherein the number of living cells per animal can be increased further, without sacrificing unnecessarily the animal, by successively removing the chamber, inoculating the cells in another chamber containing fresh nutrient medium therein and placing the latter chamber on the same animal, and (b) a method wherein the human cells that multiplied in animal body are exposed to an interferon inducer in vivo and/or in vitro to induce interferon using the same cells one or more times.

Any known interferon inducer, for example, virus, bacterium, protozoa, rickettsia, nucleic acid, endotoxin and polysaccharide can be freely used.

The formed interferon can be readily purified by known purification methods, for example, by salting-out, dialysis, filtration, centrifugation, concentration and lyophilization. If necessary, the obtained interferon preparation can be purified further by known methods such as adsorption and desorption with ion-exchanger, gel-filtration, affinity chromatography, isoelectric point fractionation and electrophoresis.

Interferon activity was determined with FL cells derived from human amnion, as described in "Protein, Nucleic Acid and Enzyme", vol. 20, no. 6, pp. 616–643 (1975), published by Kyoritsu Shuppan Co., Ltd., Tokyo, according to the conventional plaque reduction method.

The hemagglutinin titer was assayed according to the method described by J. E. Salk, ["Journal of Immunology", vol. 49, p. 87 (1944)].

Some examples for producing interferon according to the invention are described below.

EXAMPLE A

Production of interferon

EXAMPLE A-1

Adult nude mice were transplanted subcutaneously with established BALL-1 cells derived from human, and the mice were fed in the usual way for 3 weeks. About 10 g of massive tumor per nude mouse that formed subcutaneously was isolated, cut finely, suspended in saline containing trypsin to dissociate the tumor into cells, and the cells were collected by centrifugation. The cells were washed with an Eagle's minimal essential medium, at pH 7.2 and 37° C., containing 5 v/v % human serum, and resuspended to give a concentration of about $5 \times 10^6$ cells per ml. To the obtained mixture was added about 100 units per ml of partially purified human species specific interferon, and the mixture was incubated for about 2 hours, and then about 300 hemagglutinin titers per ml of Sendai virus were added and incubated for an additional 20 hours to induce interferon. The incubated mixture solution was centrifuged, about 1,000×g, at about 4° C. to remove precipitates such as cells. The obtained supernatant was dialysed against 0.1 M buffer solution, pH 2.0, containing hydrochloric acid and potassium chloride, at 4° C. for 48 hours, then dialysed against 0.01 M phosphate-buffered saline, pH 7.2, for 12 hours, and filtered carefully by membrane filtration. The filtrate was concentrated and lyophilized into an interferon powder with high activity. The interferon activity was about 20,000,000 units per nude mouse.

EXAMPLE A-2

Adult nude mice were transplanted intraperitoneally with established OUMS-20 cells derived from human, and fed in the usual way for 5 weeks. The mice were injected intraperitoneally with Newcastle disease virus which originally had a hemagglutinin titer of about 3,000 but was almost completely preinactivated by means of ultra-violet irradiation. The mice were sacrificed after 24 hours and then the ascitic fluid was harvested. The fluid was centrifuged, about 1,000×g, at 4° C. to remove precipitates such as cells. The supernatant was dialysed against 0.1 M buffer solution, pH 2.0, containing hydrochloric acid and potassium chloride, at 4° C. for 48 hours, then dialysed against 0.01 M phosphate-buffered saline, pH 7.2, for 15 hours, and filtered carefully by membrane filtration. The filtrate was concentrated to give an interferon solution with high activity. The interferon activity was about 700,000 units/10 nude mice.

EXAMPLE A-3

Newborn hamsters which received intraperitoneal injection of known rabbit antilymphocyte serum against hamster thymocytes and subcutaneous transplantation of established JBL cells derived from human were fed in the usual way for 4 weeks.

About 30 g of massive tumor per hamster formed subcutaneously was isolated and dissociated similarly as in EXAMPLE A-1. The obtained cells were washed with RPMI 1640 medium, pH 7.4 and 37° C., containing a 10 v/v % calf serum, and resuspended to give a concentration of about $2 \times 10^7$ cells per ml. To the obtained mixture solution was added 200 units per ml of partially purified interferon with human species specificity, and the mixture was incubated for about one hour. After adding about 100 hemagglutinin titers per ml of Sendai virus, the resultant mixture was incubated for an additional 16 hours to induce interferon.

Subsequently, the obtained solution was purified and concentrated similarly as in EXAMPLE A-2 to give an interferon solution with high activity. The interferon activity was about 15,000,000 units per hamster.

EXAMPLE A-4

Newborn rats were transplanted intravenously with established Namalva cells derived from human and fed in the usual way for 4 weeks.

About 50 g of massive tumor per rat formed subcutaneously was isolated and dissociated similarly as in EXAMPLE A-1.

Subsequently, the obtained cells were treated similarly as in EXAMPLE A-1 to induce interferon. The obtained interferon solution was purified and lyophilized similarly as in EXAMPLE A-1 into an interferon powder with high activity. The interferon activity was about 30,000,000 units per rat.

EXAMPLE A-5

Adult mice were subjected to X-ray irradiation at about 400 rem to weaken their immunoreactions, then were transplanted subcutaneously with established TALL-1 cells derived from human and fed in the usual way for 3 weeks.

About 10 g of massive tumor that formed subcutaneously per mouse was isolated and dissociated similarly as in EXAMPLE A-1.

The obtained cells were treated similarly as in EXAMPLE A-3 to induce interferon. The obtained interferon solution was purified and concentrated similarly as in EXAMPLE A-2 to give an interferon solution with high activity. The interferon activity was about 8,000,000 units per mouse.

EXAMPLE A-6

Established OUMS-25 human cells were transplanted subcutaneously to hamsters similarly as in EXAMPLE A-3 for 3 weeks and then transplanted intraperitoneally into 10-day-old nude mice. The nude mice were fed in the usual way for 5 weeks, anesthetized and the ascitic fluid was harvested. The fluid was centrifuged to collect the multiplied cells. The cells were washed and allowed to induce interferon similarly as in EXAMPLE A-1. The obtained interferon solution was purified and concentrated similarly as in EXAMPLE A-2 to give an interferon solution with high activity. The interferon activity was about 2,000,000 units per nude mouse.

EXAMPLE A-7

Established JBL cells derived from human were suspended in saline in 10 ml plastic cylindrical diffusion chambers fitted with membrane with pores of about 0.5 microns in diameter. The chambers were embedded intraperitoneally in adult rats.

The rats were fed in the usual way for 4 weeks and the chambers were removed.

The concentrations of the cells in the chambers were found to be about $5 \times 10^9$ cells per ml which was about $10^3$ times higher than that attained in vitro on a nutrient medium in a $CO_2$ incubator.

The cells were treated similarly as in EXAMPLE A-1 to induce interferon. The obtained interferon solution was purified, concentrated and lyophilized into an interferon powder with high activity. The interferon activity was about 30,000,000 units per rat.

EXAMPLE A-8

To the allantoic cavities of fertile white eggs, incubated 37° C. for 5 days, were transplanted NALL-1 cells derived from human, and the eggs were incubated at 37° C. for a week.

The eggs were opened and the multiplied cells were collected. The cells were treated similarly as in EXAMPLE A-1 to induce interferon. The obtained interferon solution was purified and concentrated similarly as in EXAMPLE A-2 to give an interferon solution with high activity. The interferon activity was about 400,000 units/10 fertile white eggs.

EXAMPLE A-9

The interferon powder prepared by the method in EXAMPLE A-1, was further purified by the methods, described by G. Bodo, (Symposium on Preparation, Standardization and Clinical Use of Interferon, "11th International Immunobiological Symposium", 8 & 9

June, 1977, Zagreb, Yugoslavia), i.e., adsorption and desorption with ion-exchanger, molecular weight fractionation by gel-filtration, concentration and careful filtration with membrane filter. The obtained interferon solution had an activity of $2 \times 10^6$ units per mg protein. The interferon recovery was about 40%.

The interferon obtained in EXAMPLES A-1 to A-9 can be advantageously used intact or in mixtures with one or more other substances as injections and medicines for external and internal uses for preventing and treating interferon-sensitive human diseases. The invention will be illustrated further with reference to the following experiments.

EXPERIMENT 1

Treatment of virus diseases with the interferon (Inhibition test on virus multiplication in vitro)

To monolayers of human embryonic lung cells formed by primary culture in Petri dishes, 6 cm in diameter, were added 0, 1, 10 or 100 units of the interferon prepared by the method in EXAMPLE A-9 and the obtained mixtures were incubated in a 5 v/v % $CO_2$ incubator at 37° C. for 20 hours. To the cells was added Varicella-zoster virus or human cytomegalovirus in an amount such that about 100 plaques form in the case of the interferon non-added cells. The admixture was incubated and the numbers of the plaques formed were counted.

The inhibition effect of interferon on the virus multiplication was determined using the following equation.

$$\text{Reduction in the number of plaque (\%)} = \frac{A - B}{B} \times 100$$

where A is the number of plaques in the case of the interferon non-addition, and B is the number of plaques in the case of the interferon addition.

The results are shown in Table 1.

TABLE 1

| | Varicella-zoster virus | Human cytomegalovirus |
|---|---|---|
| 0 unit | 0% | 0% |
| 1 unit | 12% | 5% |
| 10 units | 53% | 64% |
| 100 units | 91% | 84% |

As is clear from the results in Table 1, the interferon of the invention inhibits multiplication of disease-causing viruses.

No abnormality was noted in the cultured human cells when the interferon was added to the cells.

EXPERIMENT 2

Treatment of non-viral diseases with the interferon (1) Inhibition test on multiplication of tumor cells in vitro To RPMI 1640 medium supplemented with 15 v/v % fetal calf serum the interferon prepared by the method in EXAMPLE A-9 was added to give concentrations of 30, 300 and 3,000 units per ml, respectively. The resultants were inoculated with human tumor cells to give a concentration of $5 \times 10^5$ cells per ml and incubated in 5 v/v % $CO_2$ incubators at 37° C. for 5 days. Then, the number of the cells per ml medium was counted. Controls, prepared as above with the exception that the interferon was preinactivated by heating at 100° C. for 30 min., were incubated similarly.

The inhibition effect of the interferon on the cell multiplication was determined by the following equation.

$$\text{Inhibition of cell multiplication (\%)} = \frac{(A - 5 \times 10^5) - (B - 5 \times 10^5)}{(A - 5 \times 10^5)} \times 100$$

where A is the number of cells in the control, and B is the number of cells in the interferon-treated test.

The results are shown in Table 2.

TABLE 2

| Interferon concentration (units per ml) | Human tumor cells | | | |
|---|---|---|---|---|
| | BALL-1 | TALL-1 | NALL-1 | JBL |
| 30 | +18% | +12% | +21% | +19% |
| 300 | +57% | +61% | +63% | +54% |
| 3,000 | +88% | +82% | +85% | +91% |

As is clear from the results in Table 2, the interferon inhibits extremely the multiplication of tumor cells such as BALL-1 cell, TALL-1 cell, NALL-1 cell and JBL cell and the interferon is effective in the concentration in the range of 30 to 3,000 units per ml.

(2) Inhibition test on multiplication of tumor cells in vivo

The test was carried out with 8 nude mice, about two-months old. TALL-1 cells (tumor cells), $7.5 \times 10^6$ cells per nude mouse, were transplanted subcutaneously in all mice. From the third day of the transplantation, 4 mice received intraperitoneally 20 dosages of the interferon prepared by the method in EXAMPLE A-3; one dosage 10,000 units per nude mouse, three dosages a week. After the transplantations, the mice were fed for 48 days and sacrificed. The wet weights of the formed tumors in the mice were weighed. The remaining 4 mice, used as controls, were fed and sacrificed similarly except that they did not receive the interferon. The wet weights of the formed massive tumors were weighed.

The results are shown in Table 3.

TABLE 3

| | Control | Interferon-treated test |
|---|---|---|
| 1 | 5.8 g | 1.6 g |
| 2 | 8.8 g | 1.1 g |
| 3 | 4.3 g | 0 g |
| 4 | 7.5 g | 0 g |
| Average weight | 6.6 g | 0.7 g |

(3) Inhibition test on multiplication of tumor cells in vivo

The test was carried out with 8 nude mice, about two-months old.

JBL cells (tumor cells), $10^7$ cells per nude mouse, were transplanted subcutaneously in all mice. From the third week of the transplantation, 4 mice received intraperitoneally 8 dosages of the interferon prepared by the method in EXAMPLE A-2; one dosage 1,000 units per nude mouse, two dosages a week. After the transplantation, the mice were fed for 42 days and sacrificed. The wet weights of the formed tumors were weighed. The remaining 4 mice, used as controls, were fed and sacrificed similarly except that they did not receive the interferon. The wet weights of the formed tumors were weighed.

The results are shown in Table 4.

TABLE 4

| | Control | Interferon-treated test |
|---|---|---|
| 1 | 4.5 g | 0.7 g |
| 2 | 4.9 g | 1.4 g |
| 3 | 17.1 g | 0.9 g |
| 4 | 20.3 g | 0.7 g |
| Average weight | 11.7 g | 0.9 g |

As is clear from the results in Table 3 and 4, the interferon inhibits the formation of human massive tumor in mice, and that even if the tumor is formed, its weight is much less than those of the controls. In comparison with the controls, the interferon treated-nude mice had a stronger appetite and were more physically active.

EXPERIMENT 3

Acute toxity test

Acute toxity test was carried out with 20-days old mice by injecting intraperitoneally the interferon solution prepared by the method in EXAMPLE A-9. The result gave an extremely low toxicity; $LD_{50}$ of more than 20,000,000 units per kg when injected intraperitoneally into mice.

As is clear from the experiments described above, the interferon-sensitive diseases mentioned in the invention are those which can be prevented or treated with the interferon in the invention; i.e., viral diseases, such as epidemic keratoconjunctivitis, herpetic keratitis, influenza, rubella and serum hepatitis, and non-viral diseases, such as certain types of cancer.

Medicines or therapeutic agents for interferon-sensitive diseases which contain interferon are preparable in various forms and phases according to the final uses, i.e., liquid preparations such as nebula, eyewash, nose drop, gargle and injection, paste preparations such as ointment, and solid preparations such as in powder, granule and tablet.

The preparations are sufficiently effective for preventing and treating the interferon-sensitive diseases if they contain, generally, 1 to 10,000,000 units of interferon per g. If necessary, the preparations can be incorporated with one or more members of a group comprising therapeutic agent, vehicle, filler and stabilizer.

Some embodiments of interferon-containing preparations will be described.

EXAMPLE B

Preparations

EXAMPLE B-1

A liquid preparation

A liquid preparation was prepared with saline and the interferon obtained by the method in EXAMPLE A-1 to give an interferon concentration of 500 units per ml. The preparation is suitable as nebula, eyewash, nose drop and gargle for preventing and treating viral diseases; particularly, epidemic keratoconjunctivitis and influenza.

EXAMPLE B-2

An injection solution

An injection solution was prepared with saline and the interferon obtained by the method in EXAMPLE A-9 to give an interferon concentration of 100,000 units per ml.

The injection solution is suitable for treating all interferon-sensitive diseases such as viral and certain tumoral diseases.

EXAMPLE B-3

An injection solution

An injection solution was prepared with 500 ml of a 10 w/v % aqueous maltose solution, 1,000,000 units of the interferon prepared by the method in EXAMPLE A-5 and 10 mg of cyclophosphamide. The injection solution is suitable for treating, particularly, tumoral diseases.

EXAMPLE B-4

An injection solution

An injection solution was prepared with 100 ml of a 10 w/v % aqueous maltose solution, 500,000 units of the interferon prepared by the method in EXAMPLE A-6 and 2 mg of mitomycin C. The injection solution is suitable for treating, particularly, certain tumoral diseases.

EXAMPLE B-5

An ointment

An ointment was prepared in the usual way by mixing the interferon powder prepared by the method in EXAMPLE A-4 with vaseline and liquid paraffin to give an interferon activity of 10,000 units per g. The preparation is suitable for treating viral skin diseases.

EXAMPLE B-6

Tablets

Tablets were prepared in the usual way by tabletting a mixture of the interferon powder obtained by the method in EXAMPLE A-7, starch and maltose to give an interferon activity of 1,000 units per tablet (100 mg). The tablets are suitable for preventing and treating viral diseases of the digestive system.

EXAMPLE B-7

A liquid preparation

A liquid preparation for oral administration was prepared with 10 ml of a 10 w/v % aqueous maltose solution, 200,000 units of the interferon obtained by the method in EXAMPLE A-8 and 5 mg of methotrexate. The preparation is suitable for treating, particularly, certain tumoral diseases.

What we claimed is:

1. In the process for producing human-specific interferon comprising cultivating established human cells, exposing the resultant cells to the action of an interferon inducer to induce the interferon, and collecting and purifying the interferon, the improvement whereby the quality and quantity of interferon is greatly increased, comprising, as said cultivating step, transplanting the established human cells into a non-human warm-blooded animal body, and wherein said exposing step is in vivo or in vitro.

2. In the process for producing human-specific interferon comprising cultivating established human cells, exposing the resultant cells to the action of an interferon inducer to induce the interferon, and collecting and purifying the interferon, the improvement whereby the quality and quantity of interferon is greatly increased, comprising, as said cultivating step, inoculating the established human cells onto a nutrient medium in a diffusion chamber having pores of about $10^{-7}$ to $10^{-5}$ m in diameter, placing the diffusion chamber in or on the body of a non-human warm-blooded animal such that the nutrient body fluids of the animal have access to the chamber, and multiplying the cells while allowing the animal to supply the cells with its nutrient body fluid.

3. A process as set forth in claims 1 or 2, wherein the established cells are leucocytes.

4. A process as set forth in claim 3, wherein the established leucocyte cells are Namalva cells, TALL-1 cells, BALL-1 cells, NALL-1 cells or JBL cells.

5. A process as set forth in claims 1 or 2, wherein the warm-blooded animal is mammalian.

6. A process as set forth in claims 1 or 2, wherein the human cells are multiplied for 1 to 20 weeks.

7. A process as set forth in claims 1 or 2, wherein the resultant cells are exposed to the action of interferon inducer in a concentration of about $10^5$ to $10^8$ cells per ml.

8. A process as set forth in claims 1 or 2, wherein the resultant cells are exposed to the action of interferon inducer at about 20° to 40° C.

* * * * *